(12) United States Patent
Devaux et al.

(10) Patent No.: US 10,029,975 B2
(45) Date of Patent: Jul. 24, 2018

(54) METHOD FOR THE PRODUCTION OF BIO-SOURCED ACRYLIC ACID (71) Applicant: Arkema France, Colombes (FR)

(72) Inventors: Jean-Francois Devaux, Soucieu en Jarrest (FR); Michel Fauconet, Valmont (FR); Sandeep Jain, Paris (FR); Stephen Tlatlik, Dortmund (DE)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 15/118,134

(22) PCT Filed: Feb. 16, 2015

(86) PCT No.: PCT/FR2015/050371
§ 371 (c)(1),
(2) Date: Aug. 11, 2016

(87) PCT Pub. No.: WO2015/124856
PCT Pub. Date: Aug. 27, 2015

(65) Prior Publication Data
US 2017/0166507 A1    Jun. 15, 2017

(30) Foreign Application Priority Data
Feb. 19, 2014 (FR) ..................... 14 51315

(51) Int. Cl.
C07C 51/25 (2006.01)
C07C 51/44 (2006.01)
C07C 51/43 (2006.01)
C07C 45/52 (2006.01)

(52) U.S. Cl.
CPC ............ C07C 51/252 (2013.01); C07C 45/52 (2013.01); C07C 51/43 (2013.01); C07C 51/44 (2013.01)

(58) Field of Classification Search
CPC ....... C07C 51/252; C07C 45/52; C07C 51/43; C07C 51/44; C07C 51/487; C07C 67/08; C07C 67/54; C07C 67/58; Y02P 20/582
See application file for complete search history.

(56) References Cited

U.S. PATENT DOCUMENTS

| | | | |
|---|---|---|---|
| 5,387,720 A | 2/1995 | Neher et al. | |
| 6,498,272 B1 | 12/2002 | Schroder et al. | |
| 6,646,161 B1 | 11/2003 | Eck et al. | |
| 7,151,194 B2 | 12/2006 | Ueno et al. | |
| 7,396,962 B1 | 7/2008 | Dubois et al. | |
| 7,612,230 B2 | 11/2009 | Shima et al. | |
| 7,655,818 B2 | 2/2010 | Dubois et al. | |
| 8,178,719 B2 | 5/2012 | Shima et al. | |
| 8,212,070 B2 | 7/2012 | Dubois et al. | |
| 8,242,308 B2 | 8/2012 | Ho et al. | |
| 8,252,960 B2 | 8/2012 | Dubois et al. | |
| 8,378,136 B2 | 2/2013 | Dubois | |
| 8,404,887 B2 | 3/2013 | Moriguchi et al. | |
| 8,530,700 B2 | 9/2013 | Ho et al. | |
| 8,748,545 B2 | 6/2014 | Devaux et al. | |
| 9,371,261 B2 | 6/2016 | Fauconet | |
| 2009/0068440 A1 | 3/2009 | Bub et al. | |
| 2009/0134357 A1 | 5/2009 | Bub et al. | |
| 2009/0253934 A1 | 10/2009 | Ho et al. | |
| 2012/0071620 A1 | 3/2012 | Sakamoto et al. | |
| 2012/0190890 A1 | 7/2012 | Fauconet | |
| 2012/0226074 A1 | 9/2012 | Ho et al. | |
| 2012/0330058 A1* | 12/2012 | Devaux .................. C07C 45/52 562/533 |
| 2013/0053595 A1 | 2/2013 | Magatani et al. | |
| 2013/0165690 A1 | 6/2013 | Fauconet et al. | |

FOREIGN PATENT DOCUMENTS

| | | | |
|---|---|---|---|
| EP | 1 710 227 B1 | 9/2010 | |
| EP | 2 371 801 A1 | 10/2011 | |
| EP | 2 066 613 B1 | 6/2012 | |
| WO | WO2008/033687 | * | 3/2008 |
| WO | WO 2008/0336687 A2 | 3/2008 | |

* cited by examiner

Primary Examiner — Pancham Bakshi
Assistant Examiner — Mark R Luderer
(74) Attorney, Agent, or Firm — Lynn B. Morreale (57) ABSTRACT

The present invention relates to the manufacture of biobased acrylic acid from glycerol as starting material, the term "biobased acid" indicating that the acrylic acid is essentially based on a carbon source of natural origin.

13 Claims, 1 Drawing Sheet

METHOD FOR THE PRODUCTION OF BIO-SOURCED ACRYLIC ACID

CROSS-REFERENCE TO RELATED APPLICATIONS

This application is a national stage application under 35 U.S.C. § 371 of PCT/FR2015/050371, filed Feb. 16, 2015 which claims benefit to application FR14.51315, filed Feb. 19, 2014.

The work leading to the present invention benefited from financial support from the Seventh Framework Programme of the European Community by virtue of the grant agreement No. 228867.

TECHNICAL FIELD

The present invention relates to the manufacture of biobased acrylic acid from glycerol as starting material, the term "biobased acid" indicating that the acrylic acid is essentially based on a carbon source of natural origin.

A subject of the present invention is more particularly a process for recovering/purifying said acid in a compact apparatus without using organic solvent, and also a process for manufacturing acrylic acid from glycerol which integrates this recovering/purifying process. The process also has the advantage of resulting in a quality of acrylic acid capable of being subjected to a conventional ultimate purification treatment by crystallization, and of preserving the environment by limiting aqueous waste and energy consumption.

Technical Background and Technical Problem

Acrylic acid is a very important starting material which can be used directly to obtain an acrylic acid polymer or, after esterification with alcohols, to produce a polymer of the corresponding ester. These polymers are used as they are or as copolymers in fields as varied as hygiene (for example, in the production of superabsorbents), detergents, paints, varnishes, adhesives, paper, textiles, leather, etc.

Manufacturers have been developing processes for synthesizing acrylic acid for decades.

The process, which today is the most widely industrially exploited process, implements a reaction in which propylene is catalytically oxidized by means of oxygen or an oxygen-containing mixture.

This reaction is generally carried out in the gas phase, and most commonly in two steps: the first step carries out the substantially quantitative oxidation of the propylene to give an acrolein-rich mixture, and then, during the second step, the acrolein is selectively oxidized to give acrylic acid.

The reaction conditions of these two steps, carried out in two reactors in series or in a single reactor comprising the two reaction steps in series, are different and require catalysts suited to the reaction; however, it is not necessary to isolate the intermediate acrolein during this two-step process.

The starting materials used in this process result from petroleum or natural gas and, consequently, the acrylic acid consists of a non-renewable fossil carbon starting material. In addition, the processes for extracting, purifying and synthesizing the starting materials and also the processes for destroying, at the end of the cycle, the manufactured finished products based on these fossil starting materials generate carbon dioxide, the latter being, moreover, also a direct by-product of the reactions of the oxidation of propylene to give acrolein and then of acrolein to give acrylic acid. All this contributes to increasing the concentration of greenhouse gases in the atmosphere. In the context of the commitments of the majority of industrialized countries to reduce greenhouse gas emissions, it appears to be particularly important to manufacture novel products based on renewable starting material, contributing to reducing these environmental effects.

Thus, in order to limit the ecological impact of the conventional processes for producing acrylic acid, alternative processes using renewable natural starting materials, termed "biobased" processes, have recently been developed.

These are, for example, processes using glycerol (also called glycerin) as starting material. The glycerol is mainly derived from the methanolysis of vegetable oils at the same time as methyl esters which are, themselves, used in particular as fuels or combustibles in gas oil and domestic heating oil. The glycerol is available on a large scale.

The conversion of glycerol to acrylic acid is carried out in two steps, namely the obtaining of acrolein by dehydration of glycerol, which is in particular described in documents U.S. Pat. No. 5,387,720, WO 06/087083 or WO 06/087084, followed by a "conventional" oxidation of the acrolein so as to obtain acrylic acid.

The first step of the manufacture of acrylic acid from glycerol results in the same intermediate compound as the conventional process for manufacturing from propylene, namely acrolein, according to the reaction:

which is followed by the second oxidation step according to the reaction

Patent Applications EP 1 710 227, WO 2006/136336 and WO 2006/092272 describe such processes for the synthesis of acrylic acid from glycerol comprising the step of gas-phase dehydration in the presence of catalysts consisting of inorganic oxides (which may or may not be mixed) based on aluminium, titanium, zirconium, vanadium, etc., and the step of gas-phase oxidation of the acrolein thus synthesized in the presence of catalysts based on oxides of iron, molybdenum, copper, etc., alone or in combination in the form of mixed oxides.

Various studies have, moreover, been carried out more recently on new catalysts in order to optimize the gas-phase glycerol dehydration reaction (WO 2009/128555; WO 2010/046227; WO 2011/033689).

This biobased process for the synthesis of acrylic acid from glycerol is highly analogous to the process for synthesis from propylene in so far as the intermediate product, acrolein, resulting from the first step is the same, and the second step is carried out under the same operating conditions.

However, the first-step dehydration reaction is different from the propylene oxidation reaction of the usual process. Indeed, the dehydration reaction performed in the gas phase is carried out by means of solid catalysts different from those used for the oxidation of propylene, and generally using glycerol in aqueous solution. The acrolein-rich effluent resulting from the first dehydration step, intended to feed the second step of oxidation of acrolein to give acrylic acid, thus comprises a greater amount of water (linked to the glycerol load in aqueous solution and to the reaction itself), risking degradation of the second-step catalyst, and in addition exhibits substantial differences in terms of by-products (nature and content) resulting from the different reaction mechanisms involved and which are materialized through different selectivities in each of the two routes.

Improvements have been introduced in order to remove a part of the water present in the gas resulting from the first dehydration step, so as to prevent deactivation of the catalyst used in the second oxidation step by volatilization of certain constituent elements of this catalyst in the presence of water. This additional step, such as that described in Patent Application WO 08/087315 in the name of the applicant company, consists of a partial condensation of the water (generally from 20% to 95% of the water present), carried out with cooling to a temperature which makes it possible to obtain, after elimination of the condensed phase, a gas stream containing water and acrolein in a molar ratio compatible with the catalytic reaction for oxidation of the acrolein to acrylic acid, while at the same time preventing degradation of the second-stage catalyst. This is partial condensation of the water also makes it possible to simultaneously eliminate a part of the "heavy" impurities formed during the dehydration reaction.

The impurities formed during this first dehydration step are, in addition to oxygen, the nitrogen and the water introduced into the feed mixture or formed during this step, compounds which are lighter than acrolein, for instance carbon monoxide, carbon dioxide, formaldehyde, acetaldehyde, propionaldehyde and methylglyoxal, and impurities which are heavier than acrolein, for instance traces of unconverted glycerol, of acetic acid, of acrylic acid, of propionic acid and heavy compounds present in the glycerol used as starting material, and also reaction products, for instance hydroxypropionaldehyde, hydroxyacetone, phenol, products from polycondensation of glycerol, cyclic ethers of glycerol, acetals, dioxanes and dioxolanes.

The second step, namely the step of oxidation of the acrolein to give acrylic acid, is generally carried out under operating conditions similar to those used for the acrolein originating from propylene.

The gaseous mixture resulting from the $2^{nd}$ step (oxidation reaction) consists, apart from acrylic acid:
- of impurities resulting from the first reaction step which have not reacted;
- of light compounds which are noncondensable under the temperature and pressure conditions normally employed, unconverted in the $1^{st}$ step or formed in the second step: nitrogen, unconverted oxygen, carbon monoxide and carbon dioxide, which are formed in a small amount by final oxidation or continuous oxidation, by recycling, in the process;
- of condensable light compounds unconverted in the $1^{st}$ step or formed in the second step: water, unconverted acrolein, light aldehydes, for instance formaldehyde and acetaldehyde, formic acid, acetic acid or propionic acid;
- of heavy compounds: furfuraldehyde, benzaldehyde, maleic acid, maleic anhydride, benzoic acid, 2-butenoic acid, phenol and protoanemonin.

The second stage of the manufacture consists in recovering the acrylic acid contained in this gaseous effluent in order to convert it into a grade of acrylic acid compatible with its final use. Indeed, since the quality of the acrylic acid, i.e. its content of various impurities, plays a major role in the subsequent polymerization processes, manufacturers manufacturing this acrylic acid are led to involve an entire series of purification steps, taking account of the greater contents of certain impurities or of the presence of different impurities, compared with the conventional propylene oxidation process.

The first step of this recovering/purifying phase consists of extraction of the acrylic acid by countercurrent absorption in a solvent, generally water introduced by an external source and/or originating from the process. The amounts of water and of gaseous reaction mixture are such that the weight content of acrylic acid in the crude aqueous solution produced is about 40% to 80%.

Document WO 2010/031949 in the name of the applicant company describes a process for the manufacture of polymer grade acrylic acid using glycerol as starting material which is converted into acrylic acid in two steps dehydration and oxidation as previously mentioned, followed by an overall process of purification of the aqueous solution of crude acrylic acid produced, by absorption of the gaseous effluent in water. This overall process comprises a combination of steps, in particular the dehydration of the aqueous solution in the presence of a solvent which is water-immiscible but capable of forming an azeotrope with water; the elimination of light compounds, in particular acetic acid and formic acid, by distillation; the elimination of the heavy impurities by distillation, so as to obtain a "technical"-grade acrylic acid quality; the elimination of certain residual impurities, in particular the aldehydes still present, by chemical treatment.

In document WO 2011/010035, the final step of purification of the biobased acrylic acid in order to achieve a quality of acrylic acid which is usually referred to as glacial acrylic acid AAg, is a separation by fractional crystallization applied to one of the effluents resulting from the acrylic acid purification chain, it being possible for the location of this final crystallization step to depend on the initial load treated, the nature and the source of glycerol used in the process, the purity specifications to be achieved for the final acrylic acid or, finally, economic criteria.

These processes nevertheless pose a very substantial economic problem owing to the expensive energy required for the elimination of the water used as solvent for absorption (or extraction) of the acrylic acid in so far as the elimination of the water is carried out by distillation with a third azeotropic solvent, and the large number of distillation columns, the operating of which needs to be adjusted in the presence of polymerization inhibitors, in order to optimize the separation and the elimination of the by-products.

As an alternative to these processes which use water as solvent absorbing acrylic acid present in the gas stream resulting from the second step (acrolein oxidation step), documents WO 2011/114051 and WO 2011/010036 describe processes for manufacturing biobased acrylic acid which combine a step of absorption of the acrylic acid with a hydrophobic heavy solvent at the outlet of the oxidation reactor and a purification phase comprising several steps resulting in purified acrylic acid. However, such processes do not make it possible to overcome the drawbacks inherent in the use of glycerol as starting material in terms of by-products to be eliminated, and in the complexity of the steps by distillation to be combined.

There thus remains a need to have a process for manufacturing a biobased acrylic acid from glycerol which meets standards of quality that allow it to be used in the manufacture of a wide range of polymers, without, however, requiring sophisticated and therefore expensive purification.

Recently, new "solvent-free" technologies for recovering/purifying acrylic acid have appeared, involving a reduced number of purification steps and eliminating the introduction of external organic solvent.

Mention may be made, for example, of U.S. Pat. No. 6,498,272 which describes a process for preparing acrylic acid from propane and/or propylene, in which the gaseous reaction mixture is first cooled in a first section, and then sent to a single column for purification. A fractional condensation is carried out with recovery of the crude acrylic acid by side take-off, and recovery of the heavy by-products at the column bottom, which are then subjected to thermal cracking with a view to recycling to the cooling section.

In the process for producing acrylic acid described in U.S. Pat. No. 7,151,194, the gaseous reaction mixture is sent to an absorption column and brought into contact with water, so as to obtain an aqueous solution of acrylic acid, which is then distilled in the absence of azeotropic solvent, so as to obtain, at the bottom or at the side take-off of the distillation column, a stream of crude acrylic acid which is then sent to a unit for purification by crystallization.

Patent EP 2 066 613 describes a process for recovering acrylic acid without using azeotropic solvent and using only two columns for purification of the cooled gaseous reaction mixture: a) a dehydration column where the gas stream distilled at the top is condensed and returned to the dehydration column in the form of reflux so as to absorb the acrylic acid, b) and a finishing column fed by the stream from the bottom of the first column, in which i) the residual water and residual acetic acid are distilled at the top and recycled at the bottom of the first column, ii) a stream comprising the heavy by-products and acrylic acid is eliminated at the bottom so as to be optionally used for the production of acrylic esters, and iii) a stream of technical grade acrylic acid is recovered by side take-off in the form of liquid or a vapour. In this process, a part of the streams is advantageously returned to the dehydration column heaters/reboilers or used to cool the gaseous reaction mixture which makes it possible to optimize the energy needs of the process. The technical acrylic acid obtained has a purity greater than 98.5% and contains less than 0.5% of water and less than 0.4% of acetic acid. It can also be purified by crystallization so as to produce glacial acrylic acid.

The abovementioned "solvent-free" processes are suitable for the purification of a gaseous reaction mixture comprising acrylic acid, the mixture being obtained by oxidation of acrolein derived from propylene.

When the acrolein is produced by dehydration of glycerol, the gaseous reaction mixture comprises, in addition to acrylic acid, a generally greater content of water and of by-products, in particular a greater content of acetic acid (acetic acid/acrylic acid weight ratio generally >6%), and of propionic acid which comes from the oxidation of the propionaldehyde generated in large amount during the dehydration of the glycerol (propionic acid/acrylic acid weight ratio generally >0.5%).

It has thus been proposed, in document EP 2 371 801, to recover, according to a "solvent-free" process, acrylic acid prepared by oxydehydrogenation reaction of a stream comprising acrolein and propionaldehyde obtained by dehydration of glycerol. In Example 11 of said document, the gaseous reaction mixture containing acrolein and propionaldehyde is oxidized to give acrylic acid in a catalytic reactor, and the gas stream containing acrylic acid undergoes low-temperature condensation so as to recover a mixture which contains 62% of acrylic acid and 32% of water, and to eliminate the noncondensable gases. It is only in a second purification step that the acrylic acid and the water are separated by distillation, recovering, at the bottom of the column, a stream enriched in acrylic acid (86.6%) and depleted of water (10.9%), which can then undergo a crystallization step. This process is costly in terms of energy and does not make it possible to recover the acrylic acid with a good yield.

In document US 2012/0071620 relating to a method of crystallization of acrylic acid, most of the phenol and hydroxyl acetone heavy by-products are removed from the stream of acrolein produced from glycerol, before said stream is subjected to the oxidation step so as to produce a stream of acrylic acid which, after condensation, is directly subjected to the crystallization method. The problems inherent in the presence of water in a large amount in the various streams are not mentioned in said document.

Even though the prior art describes various methods that can be used in a solvent-free process for purifying acrylic acid, it cannot be established according to the prior art that the combination of these methods would make it possible to obtain with a good yield and a low energy consumption a biobased acrylic acid corresponding to user specifications, owing to the drawbacks inherent in the use of glycerol as starting material.

The Applicant Company has in fact noted that these methods cannot be applied directly to a reaction mixture containing acrylic acid obtained by oxidation of acrolein using glycerol as starting material. For example, when subjecting a gaseous stream of crude acrylic acid resulting from an ex-glycerol process, said effluent containing a water/acrylic acid weight ratio greater than 2, to a dehydration column, such as that present in the process described in document EP 2 066 613, it has not been possible to eliminate the water at the column top without simultaneously losing a substantial amount of acrylic acid, unless an oversize column is used, but this leads to an expensive investment.

A process for manufacturing biobased acrylic acid from glycerol which integrates a simplified solvent-free recovering/purifying process, and which results, on the one hand, in a quality of acrylic acid which can be subjected to a conventional final purification treatment by crystallization and, on the other hand, in exploitable streams, has now been discovered. This process is based in particular on the obtaining of a gaseous reaction effluent of crude acrylic acid which minimizes the water/acrylic acid weight ratio, making it possible to solve, upstream, most of the problems posed by the presence of water and of impurities in a solvent-free recovering/purification process.

SUMMARY OF THE INVENTION

The present invention relates firstly to a process for recovering biobased acrylic acid from a gaseous reaction mixture obtained by gas-phase oxidation of a stream containing acrolein generated by a glycerol dehydration reaction in a first reactor, characterized in that said gaseous reaction mixture comprises a water/acrylic acid weight ratio of less than 1.6, and in that the process comprises at least the following steps:

i) the gaseous reaction mixture is subjected to a dehydration in a first column, termed dehydration column, resulting in a top stream, a part of which is condensed and returned to the dehydration column in the form of reflux, and to a bottom stream;

ii) the dehydration column bottom stream is at least partly subjected to distillation in a second column, termed purification column, resulting in a top stream which is at least partly condensed and returned to the dehydration column, and in a bottom stream containing heavy compounds;

iii) a stream comprising more than 98% by weight of acrylic acid is recovered by side take-off from the purification column.

According to certain particular embodiments, the invention also exhibits one or, preferably, more of the advantageous features listed below:

the gaseous reaction mixture comprises a water/acrylic acid weight ratio of between 0.3 and 1.5 and preferably between 0.3 and 1.2 and preferably between 0.4 and 1.1;

the acrylic acid stream recovered in step iii) contains less than 1.5%, preferably less than 0.5%, more particularly less than 0.2% by weight of acetic acid, and less than 1%, preferably less than 0.5%, more particularly less than 0.3% by weight of water;

one (or more) polymerization inhibitor(s) is (are) added during the process;

the reaction mixture is precooled so as to eliminate at least a part of its sensible heat, in order to form a cooled gaseous reaction mixture;

the optionally precooled gaseous reaction mixture is partially condensed using a condenser internal to the dehydration column;

the optionally precooled gaseous reaction mixture is partly condensed using a condenser external to the dehydration column;

at least one part of the dehydration column bottom stream is sent to a heat exchanger, which may be a reboiler or cooler, before being returned to the dehydration column;

a part of the dehydration column bottom stream is brought into direct contact with the optionally precooled gaseous reaction mixture and the resulting stream is sent to step i);

at least one part of the dehydration column top stream is sent to the glycerol dehydration step;

at least one part of the dehydration column top stream is sent to the acrolein oxidation step;

at least one part of the dehydration column top stream is subjected to an oxidation treatment;

the energy produced by the treatment for the oxidation of all or part of the dehydration column top stream is used to vaporize the glycerol prior to the dehydration reaction in the first reactor;

at least one part of the dehydration column bottom stream goes into an intermediate tank before entering the purification column;

at least one part of the dehydration column bottom stream is sent to the top of the purification column;

at least one part of the dehydration column bottom stream is sent between the top and the side take-off of the purification column; the purification column top stream is at least partly, preferably totally, sent to a condenser, the stream leaving the condenser being partly or totally returned to the dehydration column;

at least one part of the purification column bottom stream is brought to a purification column heater/reboiler;

at least one part of the purification column bottom stream is exploited in an acrylic ester production unit;

at least one part of the purification column bottom stream is subjected to a step of thermal decomposition of the Michael addition derivatives so as to produce acrylic acid;

at least one part of the stream taken off from the side of the purification column is subjected to a treatment by crystallization;

at least one part of the stream taken off from the side of the purification column is subjected to a purification by distillation, optionally coupled with a crystallization treatment.

The process according to the invention makes it possible to minimize the loss of acrylic acid during the purification process, in particular at the level of the part of the stream which is not condensed at the top of the dehydration column.

The process according to the invention is advantageous in terms of energy cost, owing to the recovery of energy originating from the oxidation of acetic acid which is produced in a larger amount in a process that uses glycerol as raw material than in a process that uses propylene; furthermore, the acetic acid is in the form of a gaseous mixture which may be directly incinerated without re-vaporization of a liquid stream as in a conventional purification process using an azeotropic solvent.

These technical, and above all economic, advantages are not suggested in the prior art, and cannot be directly deduced from the combination of the existing processes.

A subject of the present invention is also a process for manufacturing biobased acrylic acid, comprising at least the following steps:

a) glycerol is subjected to a dehydration reaction in a first reactor so as to obtain an aqueous stream containing acrolein;

b) the stream resulting from step a) is subjected to a separation step, resulting in an aqueous phase depleted of acrolein and a gas stream rich in acrolein and depleted of water;

c) said stream rich in acrolein is subjected to a gas-phase catalytic oxidation reaction in a second reactor so as to obtain a gaseous reaction mixture containing acrylic acid in a water/acrylic acid weight ratio of less than 1.6, preferably between 0.3 and 1.5 and preferably between 0.3 and 1.2, and more particularly between 0.4 and 1.1;

d) said gaseous reaction mixture is subjected to the process for recovering biobased acrylic acid as defined by steps i) to iii) above;

said process being characterized in that the conditions of the separation of step b) are adjusted so as to achieve the desired water/acrylic acid weight ratio in step c).

According to one embodiment of the invention, the separation of step b) is a partial condensation carried out at a pressure of between $10^5$ and $5 \times 10^5$ Pa and preferably between $10^5$ and $2 \times 10^5$, and at a temperature of between 40° C. and 90° C., preferably between 40° C. and 70° C. and more particularly between 45 and 60° C.

The glycerol dehydration reaction is preferably carried out in the gas phase.

According to certain particular embodiments, the process for manufacturing acrylic acid according to the invention also exhibits one or, preferably, more of the advantageous features listed below, in addition to those originally mentioned for the process for recovering/purifying acrylic acid of the invention:

prior to step a), the glycerol is vaporized;

at least one part of the aqueous phase depleted of acrolein of step b) is recycled to step a);

at least part of the aqueous phase deleted of acrolein at step b) is subjected to a treatment by oxidation before being recycled to step a);

the energy produced by the treatment for oxidation of the aqueous phase depleted of acrolein of step b) is used to vaporize the glycerol prior to the dehydration reaction of step a).

The present invention makes it possible to overcome the prior art drawbacks associated with the use of a renewable material such as glycerol and/or with the complexity of the processes required to obtain a purified acrylic acid. It provides more particularly a process for the production of acrylic acid produced from glycerol in a compact apparatus, which is free of external organic solvent, while at the same time enabling optimum control of the operating conditions, energy optimization and optimization of the acrylic acid yield, and also the recycling of exploitable streams.

This can be accomplished through controlling the content of water of the gaseous reaction mixture containing the acrylic acid, subjected to the recovering/purifying process, in particular controlling the water content during the production of said reaction mixture.

Furthermore, controlling the water content is advantageously combined with the elimination of the methylglyoxal, which is an impurity generated specifically from glycerol; the presence of methylglyoxal during the step of oxidation of the acrolein-rich stream may generate acetic acid, formic acid and propionic acid and above all lead to a fouling and clogging of the catalytic oxidation bed. This problem, and also the solution provided by the present invention, have never been suggested in the prior art.

Other features and advantages of the invention will emerge more clearly on reading the detailed description which follows.

DETAILED DESCRIPTION OF THE INVENTION

The gaseous reaction mixture subjected to the process for recovering biobased acrylic acid according to the invention is obtained by gas-phase oxidation of a stream generated by a glycerol dehydration reaction according to the following reaction scheme:

$CH_2OH$—$CHOH$—$CH_2OH \rightarrow CH_2$=$CH$—$CHO$+ $2H_2O$ $CH_2$=$CH$—$CHO$+½$O_2 \rightarrow CH_2CH$—$COOH$ The application of these 2 successive reactions, involving the formation of acrolein, results in a gaseous reaction mixture essentially comprising acrylic acid, noncondensable light compounds (nitrogen, unconverted oxygen, CO, $CO_2$, argon), water generated by the dehydration reaction or present as glycerol diluent, unconverted acrolein, and various by-products which have boiling points that are lower (termed light compounds) or higher (termed heavy compounds) than those of acrylic acid, such as aldehydes, for instance formaldehyde, acetaldehyde, furfuraldehyde or benzaldehyde, or acids, for instance formic acid, acetic acid, propionic acid, maleic acid, maleic anhydride, benzoic acid or 2-butenoic acid, and other heavy compounds, for instance phenol.

According to the invention, the recovering/purification process without external organic solvent is applied to a gaseous reaction mixture comprising a water/acrylic acid weight ratio of less than 1.6, preferably between 0.3 and 1.5 and preferably between 0.3 and 1.2, and more particularly between 0.4 and 1.1.

In a step i), the gaseous reaction mixture is subjected to a dehydration in a first column, termed dehydration column, resulting in a top stream, a part of which is condensed and returned to the dehydration column in the form of reflux, and in a bottom stream.

According to the process of the invention, the gaseous reaction mixture, generally obtained as a mixture overheated to a temperature above 280° C., can be cooled directly in the dehydration column, or can be cooled prior to the dehydration step i), in particular to a temperature below 250° C., preferably below 190° C.

The purpose of step i) is to eliminate, in a top stream, most of the water present in the reaction mixture, but also the noncondensable light compounds and the condensable light compounds, in particular the acetic acid. The dehydration column operates, at least partially, as a distillation column. It is fed with the reaction mixture in its lower part. It generates a top stream comprising most of the water and light compounds, this top stream being depleted of acrylic acid, and a bottom stream comprising most of the acrylic acid with heavy by-products.

Advantageously, the dehydration column operates at atmospheric pressure or slightly above, up to $1.5 \times 10^5$ Pa.

Advantageously, the temperature in the upper part of the dehydration column is at least 40° C., preferably is between 40° C. and 80° C. The temperature of the dehydration column bottom stream preferably does not exceed 120° C.

The dehydration column top stream is partly condensed and the condensate produced is at least partly recycled to the dehydration column in the form of reflux so as to absorb the acrylic acid. The top condenser(s) may be internal or external to the dehydration column, and of tubular exchanger or plate exchanger type or any other type of exchanger known to those skilled in the art.

The gas stream leaving the top condenser(s), which contains the noncondensable compounds, and small amounts of acrylic acid and of water vapour, is partially or totally sent to a purification device such as a thermal or catalytic oxidizer, and can also be partly recycled to other steps of the process, such as the glycerol dehydration step or the acrolein oxidation step. The gas stream leaving the purification device can be discharged into the atmosphere or recycled to other steps of the process, such as the glycerol dehydration step or the acrolein oxidation step.

According to one embodiment, all of the dehydration column top stream is sent to the top condenser(s).

According to another embodiment, a part of the dehydration column top gas stream is eliminated and the other part is sent to a top condenser. The vapours are then directly cooled in the condenser or indirectly cooled in equipment which promotes contact between the gas phase and a liquid phase, which can be generated by the condensation of said vapours and/or by addition of external water.

According to one embodiment, the dehydration step comprises a cooling function in addition to the top condenser. This cooling function can be carried out by one or more heat-exchange devices located inside the column between the top and the bottom of the column, or outside the dehydration column on a sample of a liquid, gas or two-phase stream in the column or at the bottom of the column, which is then reinjected into the column after cooling, or by a combination of these techniques.

Any type of cooling device known to those skilled in the art may be used, such as tubular exchangers, plate exchangers, fin exchangers, or any type of equipment which makes it possible to bring a hot gas phase into contact with a cold liquid phase, either by direct contact of the hot gas stream with the cold liquid stream dispersed, for example by means of nozzles, or by contact through plates or packing of all types known to those skilled in the art, etc.

According to the invention, most of the water present in the gaseous reaction mixture comprising acrylic acid is eliminated during step i) without there being any excessive loss of acrylic acid in the top stream. The water content in the dehydration column bottom stream is generally less than 10%, preferably less than 7%. The acrylic acid lost, expressed by the ratio between the flow rate of acrylic acid contained in the part of the noncondensed gas stream leaving at the top of the dehydration column, which is not recycled in the process, and the flow rate of acrylic acid of the gaseous reaction mixture entering the dehydration column, is generally less than 3%, in particular less than 2%.

Advantageously, and contrary to a conventional process for recovering/purifying acrylic acid by absorption in water and dehydration using an azeotropic solvent, the acetic acid present in the gaseous reaction stream is extracted mainly in gas form, in the dehydration column top stream. It is not necessary to vaporize this stream, which is already in the gas state, before subjecting it to an oxidation treatment in an oxidizer, which is reflected by a reduction in the energy to be provided. Moreover, the energy produced during the exothermic oxidation of the mixture rich in acetic acid, which has a high thermal level, can be advantageously reused in the process, for example to vaporize the glycerol prior to the dehydration reaction in the first reactor, by recycling the hot fumes leaving the oxidizer to the glycerol vaporization step, or else in all the steps requiring heat to be transferred to a stream.

According to the invention, the dehydration column bottom stream is at least partly sent to the top of a second distillation column, termed purification column, in which a top stream and a bottom stream are separated (step ii) and from which the purified acrylic acid is taken off at the side (step iii).

As an alternative, the dehydration column bottom stream is at least partly sent between the top and the side take-off of the purification column.

The dehydration column bottom stream can partly go into an intermediate tank before entering the purification column.

According to one embodiment, a part of the dehydration column bottom stream is sent to a heat exchanger, which may be a reboiler or a cooler, and reinjected into the dehydration column, so as to constitute a bottom loop. Preferably, it is reinjected between the gaseous reaction mixture feed and the column top.

According to one embodiment, a part of the dehydration column bottom stream is brought into contact, in a liquid-vapour contact device, with the optionally precooled gaseous reaction mixture. The stream leaving this liquid-vapour contact device is sent to step i). Optionally, the dehydration column bottom liquid stream passes through a heat exchanger before being brought into contact with the gaseous reaction mixture.

The purification column is preferably a distillation column combined with a reboiler and a condenser.

The temperature and the pressure in the purification column are not critical, and can be determined in accordance with the distillation methods known in the prior art. However, preferably, the purification column operates at a pressure below atmospheric pressure, making it possible to operate at relatively low temperatures, thus preventing the polymerization of the unsaturated products present, and minimizing the formation of heavy by-products.

Advantageously, the purification column operates at a pressure ranging from 5 kPa to approximately 60 kPa, the temperature of the top stream being advantageously between 40° C. and approximately 90° C., and the temperature of the bottom stream being between 60° C. and 120° C.

According to one embodiment, the purification column top stream is at least partly, preferably totally, sent to a condenser. The stream leaving the condenser can be partly recycled to the purification column. It is advantageously partly or totally returned to the dehydration column, between the bottom and the top of the column and preferably above the gaseous reaction mixture feed. According to one embodiment, it is mixed with the dehydration column bottom loop stream.

According to another embodiment, a part or all of the stream leaving the condenser is mixed with a part of the dehydration column bottom stream and the resulting stream is brought into contact, in a liquid-vapour contact device, with the optionally precooled gaseous reaction mixture. The stream leaving this liquid-vapour contact device is sent to step i).

The purification column bottom stream comprises most of the heavy by-products, in particular Michael addition products, such as 3-acryloxypropionic acid, maleic anhydride/acid, benzoic acid, and also polymerization inhibitors.

According to one embodiment, the purification column bottom stream is at least partially sent to a purification column heater/reboiler.

According to one embodiment, the purification column bottom stream is directly used as starting material in an acrylic ester production unit, or at least partially sent to a thin film evaporator, for instance a wiped film evaporator, which makes it possible to recover the acrylic acid present in this stream, or at least partially subjected to a step of exploitation of the acrylic acid by thermal decomposition of the Michael addition derivatives contained in said bottom stream. The thin film evaporator and/or the thermal decomposition of the purification column bottom stream thus generate acrylic acid which can be used as starting material in an acrylic ester unit or can be recycled upstream of the process for recovering acrylic acid. The thermal decomposition conditions are known to those skilled in the art.

According to the process of the invention, the majority of the acrylic acid is recovered by taking off a stream of purified product from the purification column, at a side level preferably located below the feed of said column, and preferably located above the reboiler of said column. The stream of product taken off may be a liquid stream or a gas stream.

Advantageously, the stream of product taken off at the side and the purification column bottom stream are recovered according to a weight ratio ranging from 99:1 to 25:75, preferably from 98:2 to 50:50.

According to the invention, the dehydration column and the purification column may of various configurations, for example such as a column with random or structured packing or plate columns.

The dehydration column generally comprises from 5 to 50 theoretical plates, preferably from 20 to 30 theoretical plates; the purification column generally comprises from 5 to 30 theoretical plates, preferably from 8 to 20 theoretical plates. The choice of the columns and the choice of the ancillary equipment, such as heat exchangers, condensers, pumps, fluid inlets and outlets, will be easily determined according to the considerations known from the prior art.

According to the invention, the polymerization inhibitors are chosen from compounds which inhibit the acrylic acid polymerization reaction and are added in sufficient amount, known to those skilled in the art, to prevent or reduce acrylic acid polymerization. As examples of compounds that can be used, mention may be made of phenothiazine, hydroquinone, 2,2,6,6-tetramethyl-1-piperidinyloxy (Tempo) or a derivative thereof such as 4-hydroxy Tempo, soluble copper salts, and soluble manganese salts, alone or as a mixture, optionally in solution in water, in acrylic acid or in a mixture of water and acrylic acid.

The polymerization inhibitors can be introduced in various places in the apparatus for carrying out the process of the invention, in particular into the dehydration column top stream at the level of the condenser, or into the purification column top stream at the level of the condenser associated with said column, or into the stream of purified product taken off at the side of the purification column optionally after condensation when the stream taken off is in gas form.

According to one embodiment of the invention, the nature of the inhibitor varies according to the place where it is injected.

According to one embodiment of the invention, air or an oxygen-containing gas is introduced, for example into the dehydration and purification column bottoms, into the column reboilers, into the dehydration column bottom recirculation loop or at the level of the side take-off of the purification column or into the condensers.

The stream of purified product taken off at the side consists of acrylic acid with a purity of greater than 98%, preferably greater than 99%. Preferably, it contains less than 1.5%, preferably less than 0.5%, more particularly less than 0.2% by weight of acetic acid, and less than 1%, preferably less than 0.5%, and more particularly less than 0.3% by weight of water.

The process of the invention directly provides a quality of acrylic acid which corresponds to a technical grade of acrylic acid, without it being necessary for other steps to be added thereto.

Advantageously, the acrylic acid stream taken off from the purification column is treated in a crystallization apparatus, in order to produce a quality of glacial acrylic acid that can be used to produce superabsorbents.

The crystallization apparatuses are known to the person skilled in the art and can comprise crystallization steps in continuous mode or in batchwise mode or a combination of the two. The continuous crystallization can, for example, combine steps of crystallization in suspension in the liquid to be purified, separation of the crystals and of the mother liquors, melting of the crystals, and recycling of the mother liquors, without interruption of the purification process. The crystallization in batchwise mode is, on the contrary, generally carried out by means of a succession of sequential operations of crystallization, draining of the mother liquors, partial melting and further draining of mother liquors, and, finally, melting of the crystals. These batchwise crystallization operations can be carried out in the static mode, for example in a crystallizing device where the liquid to be purified is brought into immobile contact with an exchanger, or in dynamic mode, for example in a falling film crystallization device. The crystallization apparatus generally comprises one or more purification steps so as to eliminate the impurities from the acrylic acid stream. It also comprises one or more depletion steps so as to generate a stream of mother liquors which is enriched in impurities and depleted of acrylic acid. The stream of mother liquors is at least partly eliminated from the process, for example in a thermal or catalytic purification device. It can be partially recycled upstream of the process at steps i) or ii).

Another subject of the invention relates to a process for manufacturing biobased acrylic acid from glycerol, comprising at least one set of steps a) to c), resulting in the obtaining of a gaseous reaction mixture comprising a water/acrylic acid weight ratio of less than 1.6, and integrating the recovering/purifying process as described above.

A first step a) of the process consists in subjecting glycerol to a gas-phase dehydration reaction in a first reactor R1.

The dehydration reaction is a reaction which is equilibrated but promoted by a high temperature level; it is generally carried out in the gas phase in a reactor R1 in the presence of a catalyst at a temperature ranging from 150° C. to 500° C., preferably between 250° C. and 350° C., and a pressure of between $10^5$ and $5 \times 10^5$ Pa (1 and 5 bar). It can also be carried out in the liquid phase; in this case, the temperature is between 150° C. and 350° C. at a pressure ranging from $5 \times 10^5$ to $100 \times 10^5$ Pa. This first step is preferably carried out in the gas phase.

It can also be carried out in the presence of oxygen or of an oxygen-containing gas as described in Applications WO 06/087083 and WO 06/114506. In this case, the amount of oxygen is chosen so as to be outside the inflammability range at any point of the equipment. The molar ratio between the molecular oxygen and the glycerol is generally about from 0.1 to 1.5, preferably from 0.3 to 1.0.

The dehydration reaction can also be carried out in a reaction medium comprising a gas phase containing from 1 to 3000 ppm of an acid compound within the meaning of the Pearson classification, chosen, for example, from $SO_3$, $SO_2$ and $NO_2$.

The stream feeding the dehydration reactor R1 may be, for example, commercial crude glycerol (glycerin), i.e. typically containing 80-90% of glycerol, 1% to 10% of salts, 1% to 4% of non-glycerin organic substances, including methanol, and 3% to 15% of water. Advantageously, use is made of desalted glycerol, which can be obtained from crude glycerol by any means known to those skilled in the art, for instance distillation under reduced pressure or flash distillation under reduced pressure or separation using ion-exchange resins as described, for example, in Application EP 1 978 009. It is also possible to start from salt-free glycerin obtained by processes for the transesterification of oils catalysed by heterogeneous catalysts. It is also possible to use refined glycerin with a purity of greater than 98%, 99% or 99.5%.

Advantageously, the stream feeding the dehydration reactor R1 also contains inert compounds, such as nitrogen, argon, carbon monoxide, carbon dioxide or water. The weight ratio, at the inlet of the dehydration reactor, between the water and the glycerol is between 1/100 and 10/1 and preferably between 1/4 and 2/1.

The glycerol dehydration reaction is generally carried out on solid acid catalysts. The catalysts which are suitable are homogeneous or multiphase materials which are insoluble in the reaction medium and which have a Hammett acidity, denoted $H_0$, of less than +2. As indicated in U.S. Pat. No. 5,387,720 which makes reference to the article by K. Tanabe et al in "Studies in Surface Science and Catalysis", Vol. 51, 1989, chap 1 and 2, the Hammett acidity is determined by amine titration using indicators or by adsorption of a base in the gas phase.

These catalysts can be chosen from natural or synthetic siliceous materials or acid zeolites; mineral supports, such as oxides, coated with mono-, di-, tri- or polyacidic inorganic acids; oxides or mixed oxides, or alternatively heteropolyacids or heteropolyacid salts.

These catalysts may in particular consist of a heteropolyacid salt in which protons of said heteropolyacid are exchanged with at least one cation chosen from the elements belonging to Groups I to XVI of the Periodic Table of Elements, these heteropolyacid salts containing at least one element chosen from the group comprising W, Mo and V.

Among the mixed oxides, mention may particularly be made of those based on iron and on phosphorus and those based on caesium, phosphorus and tungsten.

The catalysts are in particular chosen from zeolites, Nafion® composites (based on fluoropolymer sulphonic acid), chlorinated aluminas, phosphotungstic and/or silicotungstic acids and acid salts, and various solids of metal oxide type, such as tantalum oxide $Ta_2O_5$, niobium oxide $Nb_2O_5$, alumina $Al_2O_3$, titanium oxide $TiO_2$, zirconia $ZrO_2$, tin oxide $SnO_2$, silica $SiO_2$ or silicoaluminate $SiO_2$—$Al_2O_3$, impregnated with acid functions such as borate $BO_3$, sulphate $SO_4$, tungstate $WO_3$, phosphate $PO_4$, silicate $SiO_2$, or molybdate $MoO_3$, or a mixture of these compounds.

The previous catalysts may in addition comprise a promoter such as Au, Ag, Cu, Pt, Rh, Pd, Ru, Sm, Ce, Yt, Sc, La, Zn, Mg, Fe, Co, Ni, or montmorillonite.

The preferred catalysts are phosphate zirconias, tungsten zirconias, siliceous zirconias, titanium or tin oxides impregnated with tungstate, phosphotungstate or silicotungstate, phosphate aluminas or silicas, heteropolyacids or heteropolyacid salts, iron phosphates or boron phosphates or aluminium phosphates and iron phosphates or boron phosphates or aluminium phosphates comprising a metal promoter or a rare earth element.

The glycerol dehydration reaction can also be carried out in the presence of an amount of hydrogen ranging from 0.1% to 10% by volume relative to the reaction mixture, and in this case, in the presence of a catalyst chosen from those described in Application US 2008/018319.

For the dehydration reaction, one or more fixed bed, moving bed, fluidized bed or circulating fluidized bed reactors R1, or reactors R1 in a configuration as modules (sheets or pans), is (are) used. The contact time expressed in seconds is the ratio between the volume of the catalyst bed and the volume of the gaseous reagents sent per second. The average temperature and pressure conditions which exist in a bed can vary depending on the nature of the catalyst, the nature of the catalytic bed and the size of the catalysts. Generally, the contact time is from 0.1 to 20 seconds and preferably from 0.3 to 15 seconds.

As far as the glycerol dehydration catalysts have a tendency to become deactivated after a few hours or after a few days, the catalyst used must be continuously or periodically regenerated.

In the case of a circulating fluidized bed or of a mobile bed, partially deactivated catalyst is extracted from the reaction zone R1 so as to be sent to a reaction compartment R1a where it is flushed with an oxygen-containing regenerating gas stream.

When the catalyst is immobile, the apparatus comprises one (or more) reactor(s) R1a which contain(s) the same catalyst as the reactor(s) R1. The reactor(s) R1a is (are) flushed with an oxygen-containing regenerating gas stream. Periodically, the (one of the) reactor(s) R1a and the (one of the) reactor(s) R1 exchange their roles by means of valve switching making it possible to exchange the feed stream containing glycerol and the regenerating stream containing oxygen, that is to say the reactor which was in regeneration mode is fed with glycerol in order to produce acrolein and the reactor which was in reaction mode is fed with the oxygen-containing regenerating gas in order to regenerate the catalyst.

The oxygen-containing regenerating gas contains an oxygen concentration typically of between 0.1% and 30%, preferably between 1% and 21%, and also inert gases such as nitrogen, water, CO, $CO_2$ or argon. The temperature of the reactor(s) R1a may be between 280 and 500° C. and preferably between 300 and 450° C.

When the feeds are periodically exchanged, the oxygen concentration in the regenerating stream and/or the temperature of the reactor may be increasing during a regenerating cycle. The stream leaving the reactor(s) R1a can be partly or totally mixed with the stream of the reactors R1, or partly returned to the inlet of the reactors R1a or R1, or sent to a thermal or catalytic oxidizer.

Prior to step a), the glycerol stream feeding the dehydration reactor can be subjected to a vaporization step using hot gases resulting, for example, from an oxidation treatment carried out on the dehydration column top stream in the apparatus for recovering/purifying the acrylic acid, or on the aqueous phase depleted of acrolein, formed during step b) of the process of the invention.

After step a), an aqueous stream is obtained, which may be a liquid or gas stream, containing the acrolein formed, water, unreacted glycerol, and by-products such as hydroxypropanone, propanaldehyde, acetaldehyde, formaldehyde, methylglyoxal, acrylic acid, propionic acid, acetic acid, formic acid, acetone, phenol, products of addition of acrolein with glycerol, glycerol polycondensation products, cyclic ethers of glycerol, and also light compounds such as nitrogen, oxygen, carbon monoxide and carbon dioxide. Some of these products are heavy compounds, others are light compounds which are condensable. Others are light compounds which are noncondensable under the temperature and pressure conditions normally used.

Compared with a conventional process for oxidation of propylene to give acrolein, the water content in the stream resulting from the first step for synthesis of acrolein is high owing to the glycerol load (which may contain water) and to the reaction itself (dehydration), and to recycling of streams which may contain water.

Furthermore, some by-products present in the stream resulting from step a), in particular acetaldehyde or propanaldehyde which may subsequently generate acetic acid and propionic acid respectively, are in a greater amount than in a stream of acrolein derived from propylene. Moreover, the presence of by-products undetected in a stream of acrolein derived from propylene, such as methylglyoxal, was detected in this stream resulting from the first step a). Methylglyoxal proves to be a detrimental impurity in the process for manufacturing acrylic acid, since it is a source of acetic acid, of formic acid and of propionic acid during the step for oxidation of acrolein to give acrylic acid.

In step b) of the process according to the invention, the stream resulting from the glycerol dehydration step a) is subjected to a separation step which results in this stream being separated into a gas phase enriched in acrolein and depleted of water and a liquid phase rich in water and depleted of acrolein. This separation step is, for example, a partial condensation, described for example in document WO 08/087315 in the name of the applicant company. It may also be a more complex method such as that described, for example, in application EP 2 100 872.

This step b) is carried out in a separation unit which may be a condensation apparatus such as an absorption column optionally coupled to an evaporator, a heat exchanger, a condenser, a dephlegmator, and also any item of equipment well known to those skilled in the art which makes it possible to carry out a partial condensation of an aqueous stream.

Preferably, this separation unit will comprise a packed column coupled to a top condenser.

Surprisingly, it has been observed that, by adjusting the particular separation conditions in step b), in particular the partial condensation temperature and pressure, it is possible to obtain, in step c), a stream of crude acrylic acid compatible with the recovering/purifying process described above. Furthermore, it has also been observed, surprisingly, that these particular conditions make it possible to greatly reduce the methylglyoxal content in the acrolein-enriched stream in addition to the elimination of most of the water and heavy by-products in the acrolein-depleted liquid phase. The additional formation of by-products derived from the presence of methylglyoxal is thus prevented during the step for oxidation of acrolein to give acrylic acid of step c).

Generally, the separation of step b) is carried out at a pressure ranging from $10^5$ to $5\times10^5$ Pa and preferably between $10^5$ and $2\times10^5$ Pa.

The separation of step b) is carried out at a temperature of between 40° C. and 90° C., preferably between 40° C. and 70° C., and more particularly between 45 and 60° C.

It has in particular been noted that, with a temperature which is too high, above 90° C., the crude acrylic acid stream leaving step c) is not compatible with the recovering/purifying process as defined in steps i) to iii) because of a water content which is too high. Furthermore, with a temperature which is too low, below 40° C., the acrylic acid yield of the process is not optimal because of the loss of acrolein in the water-rich liquid phase.

Those skilled in the art will be able, by simulation, to make provision for the adjustments in pressure and in temperature of this step b) in order for the water/acrylic acid ratio on leaving step c) to be within the limits of the present invention.

The aqueous phase depleted of acrolein of step b) can be recycled at the level of the dehydration reactor, either directly, or after purification by distillation or by oxidation. Flushing of this loop will be envisaged in order to eliminate the water produced by the reaction and that possibly provided by the glycerol load.

According to step c) of the process according to the invention, the gas phase rich in acrolein is subjected to a catalytic oxidation reaction in a second reactor R2 so as to obtain a crude gaseous reaction mixture containing acrylic acid in a water/acrylic acid weight ratio of less than 1.6, preferably between 0.3 and 1.5 and preferably between 0.3 and 1.2, and more particularly between 0.4 and 1.1.

The reaction for oxidation of acrolein to give acrylic acid in step c) is carried out in the presence of molecular oxygen or of a mixture containing molecular oxygen, at a temperature ranging from 200° C. to 350° C., preferably from 250° C. to 320° C., and at a pressure ranging from 1 to 5 bar in the presence of an oxidation catalyst. All types of catalysts well known to those skilled in the art for this reaction are used as oxidation catalysts. Generally, solids containing at least one element chosen from the list Mo, V, W, Re, Cr, Mn, Fe, Co, Ni, Cu, Zn, Sn, Te, Sb, Bi, Pt, Pd, Ru and Rh, present in metal form or in oxide, sulphide or phosphate form, are used. In particular, use is made of formulations containing Mo and/or V and/or W and/or Cu and/or Sb and/or Fe as main constituents.

The oxidation reactor R2 can operate as a fixed bed, as a fluidized bed or as a circulating fluidized bed. It is also possible to use a plate exchanger with a modular arrangement of the catalyst as described in documents EP 995491, EP 1 147 807 or US 2005/0020851.

The gaseous reaction mixture obtained at the outlet of the reactor R2 can be sent directly to the compact apparatus for recovering/purifying the acrylic acid comprising a dehydration column and a purification column operating under the conditions described above.

In order to obtain a reduced propionic acid content in the purified acrylic acid stream obtained after the recovering/purifying process according to the invention, a step of propanal elimination by catalytic reaction can be carried out on the acrolein stream between step a) and step b) or between step b) and step c). This propanal elimination step is described, for example, in document WO 12/101526 in the name of the Applicant Company.

BRIEF DESCRIPTION OF THE DRAWING

The invention is illustrated by the following examples with reference to the appended FIG. 1 which represents a simplified scheme of the principle of the process for manufacturing acrylic acid from glycerol according to the invention.

EXAMPLES

Figure 1:
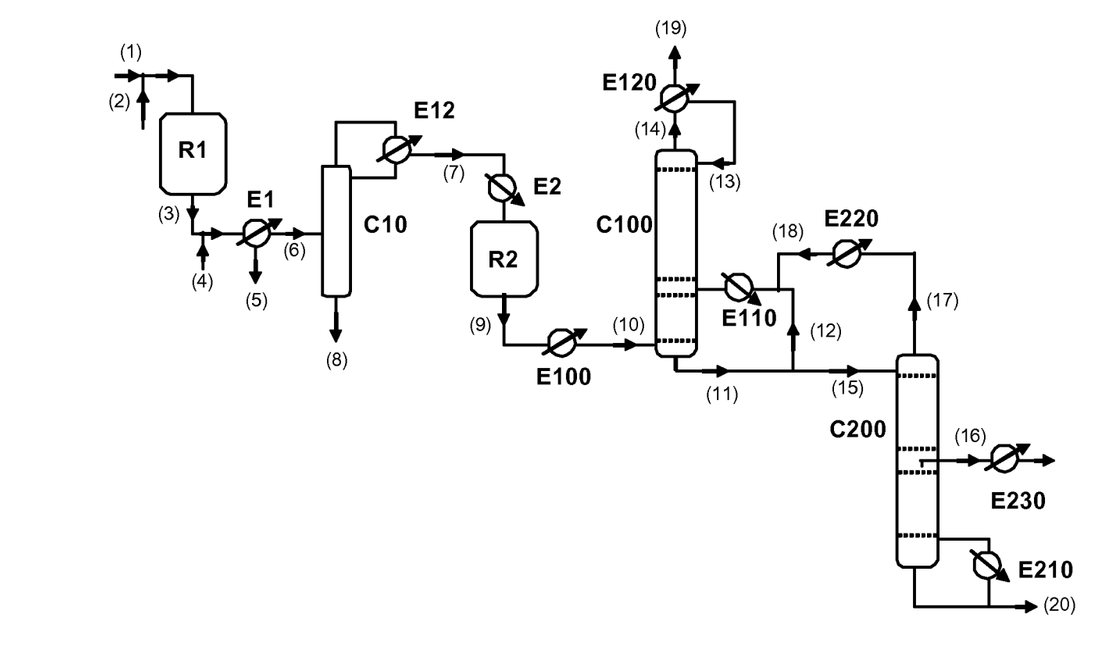

Simulations using the ASPEN software were used to illustrate the process according to the invention. The percentages are expressed as percentages by weight. The process, shown schematically in FIG. 1, comprises the following steps:

a step of vaporization of liquid glycerol (1) by a hot gas stream (2), a step of reaction for catalytic dehydration of the glycerol to give acrolein, carried out in a reactor R1 containing the dehydration catalyst which generates a stream (3), a step of regeneration of the dehydration catalyst carried out in a reactor (not represented in FIG. 1) which generates a gas stream (4) mixed with the stream (3), a cooling step during which the majority of the heavy compounds contained in the reaction gases resulting from the dehydration step are condensed, in an exchanger E1, generating a liquid stream (5) and a gas stream (6), a step of partial condensation of the water contained in the noncondensed gases (6), in a column C10, equipped at the top with a condenser (E12) which makes it possible to reflux, at the top of the column, all of the liquid stream condensed. A gas stream (7) depleted of water is taken off at the outlet of E12 and a liquid stream (8) containing predominantly water is taken off at the bottom of C10, a step of reaction for catalytic oxidation of the acrolein to give acrylic acid, carried out in a reactor R2 containing an oxidation catalyst and fed with the gas stream (7) preheated in an exchanger E2, a step of cooling the acrolein oxidation reaction gas (9) in an exchanger E100, a separation step in a dehydration column C100 with an efficiency of 24 theoretical plates. This column consists of two sections: a lower condensation section and an upper rectification section. The gaseous mixture (10) derived from E100 is fed at the bottom of the condensation section. The liquid stream (11) extracted at the bottom of the column is partially recycled (12), through an external exchanger E110, to the top of the condensation section. The upper rectification section receives, at the bottom, the noncondensed gas stream originating from the lower condensation section and, at the top, a liquid stream (13)

originating from the partial condensation, in an exchanger E120, of the gas stream (14) extracted at the top of the column C100, a step of purification of the stream (15) originating from the bottom of the dehydration column C100 in a purification column C200 which has 16 theoretical plates and is equipped with a boiler E210 at the bottom, with a condenser E220 at the top and with a system for side take-off of the gas stream. This column consists of two sections: a lower section (3 theoretical plates) located under the side take-off plate and an upper part (13 theoretical plates) located above the side take-off plate. The column is fed at the top with the liquid stream (15). The gas stream (16) taken off at the side is condensed in an exchanger E230. The gas stream (17) at the top of the column is condensed in the exchanger E220 to give a liquid stream (18) which is directly returned, without reflux in the column C200, into the C100 column bottom stream recirculation loop through the exchanger E110. The liquid stream (20) extracted at the bottom of the column C200 is a stream rich in acrylic acid also containing heavy compounds and polymerization inhibitors.

In the step of reaction for catalytic dehydration of the glycerol to give acrolein, the glycerol ((1), 11 T/h) is vaporized in the presence of a hot gas stream (2) so as to form the mixture (glycerol (18.3%), water (18.5%), oxygen (3.2%), $CO_2$ (10.1%), nitrogen (49.9%)) for feeding the reactor R1.

The stream (3) leaving the reactor R1 comprises predominantly 8.1% of acrolein, 25.6% of water and 63.4% of noncondensable compounds. This reaction gas is mixed with the gas stream (4).

The gaseous mixture obtained is cooled from 290° C. to 160° C. in the exchanger E1, and the condensed liquid stream (5) consists essentially of heavy products and only 0.25% of the water contained in the initial gas stream.

At the top of column C10 operating at an absolute pressure of 1670 hPa, the temperature in the exchanger E12 is set so as to condense a variable part of the water contained in the gas stream, according to the conditions described in Table 1.

The gas stream recovered in the exchanger E12 (7) is sent as feed for the reactor R2 for oxidation of the acrolein to give acrylic acid, after preheating in the exchanger E2 to a temperature of 240° C. The compositions at the outlet of the oxidation reactor vary according to examples and are reported in Table 1.

The column C100 operates at an absolute pressure of 1130 hPa and the column C200 at a pressure of 120 hPa.

For a rigorous comparison of the performance levels obtained under the various conditions of Examples 1 to 4 described in Table 1, restrictions were imposed on the operating parameters of the purification so as to obtain the same quality of purified product with temperature conditions making it possible to prevent the generation of polymerization. Thus, the cooling temperature in E100 and the heating temperature in E110 are adjusted so as:

to obtain a purified acrylic acid stream extracted by side take-off from the column C200 having an acrylic acid titer of at least 99%, containing a maximum of 500 ppm of acetic acid and less than 1000 ppm of water;

not to exceed 95° C. in the stream (11) at the bottom of column C100, so as to limit the formation of acryloxypropionic acid and acrylic acid polymers.

At the top of column C100, the gas stream (14) is condensed at the minimum temperature which makes it possible to simultaneously obtain:

a purified acrylic acid stream (16) extracted by side take-off from the column C200, which meets the same criterion of quality described above (less than 500 ppm of acetic acid and 1000 ppm of water);

a minimal loss of acrylic acid entrained at the top in the noncondensed gas (19).

In all of the examples, the purified acrylic acid stream obtained by side-takeoff from C200 has a temperature of 91° C., and the purity objective is achieved.

The acrylic acid losses in the purification steps refers to the ratio between the flow rate of acrylic acid in the gas stream (19) at the top of the column C100 and the flow rate of acrylic acid in the stream (9) at the outlet of the reactor R2.

The acrylic acid recovery yield is equal to 100% minus the acrylic acid losses.

The operating parameters and results of the examples are collated in Table 1;

Example 1 (According to the Invention)

purification of a gaseous reaction mixture of acrylic acid at a water/acrylic acid weight ratio of 1.09.

The acrylic acid recovery yield is 98.1%.

Example 2 (According to the Invention)

purification of a gaseous reaction mixture of acrylic acid at a water/acrylic acid weight ratio of 0.55.

The acrylic acid recovery yield is 99.9%.

Example 3 (According to the Invention)

purification of a gaseous reaction mixture of acrylic acid at a water/acrylic acid weight ratio of 0.41.

The acrylic acid recovery yield is 99.9%.

Example 4 (Comparative)

purification of a gaseous reaction mixture of acrylic acid at a water/acrylic acid weight ratio of 1.84.

The acrylic acid recovery yield is only 86.2%.

TABLE 1

| Stream | Parameters | Units | Examples | | | |
| --- | --- | --- | --- | --- | --- | --- |
| | | | 1 | 2 | 3 | 4 |
| Condensation C10-E12 | | | | | | |
| (7) | Temperature | ° C. | 65 | 52 | 47 | 75 |
| (8) | Condensed stream flow rate | T/h | 11.2 | 14.7 | 15.7 | 6.1 |
| (8) | Concentration water | % by weight | 95.3% | 96.1% | 96.3% | 93.2% |

TABLE 1-continued

| Stream | Parameters | Units | Examples 1 | 2 | 3 | 4 |
|---|---|---|---|---|---|---|
| | Outlet R2 | | | | | |
| (9) | R2 outlet flow rate | T/h | 65.9 | 61.9 | 60.5 | 71.1 |
| (9) | Water | % by weight | 9.4% | 5.0% | 3.9% | 14.9% |
| (9) | Acrolein | % by weight | 0.04% | 0.04% | 0.04% | 0.03% |
| (9) | Acrylic acid | % by weight | 8.7% | 9.2% | 9.4% | 8.1% |
| (9) | Acetic acid | % by weight | 1.1% | 1.2% | 1.1% | 1.1% |
| (9) | $O_2$ | % by weight | 1.7% | 1.8% | 2.2% | 1.9% |
| (9) | Water/acrylic add weight ratio | | 1.09 | 0.55 | 0.41 | 1.84 |
| | Outlet E100 | | | | | |
| (10) | Temperature | °C. | 185 | 180 | 180 | 185 |
| | Top C100 | | | | | |
| (17) | Temperature E120 | °C. | 60 | 49 | 45 | 69 |
| | Bottom C100 | | | | | |
| (11) | C100 bottom temperature | °C. | 93 | 88 | 88 | 94 |
| (15) | Bottom take-off flow rate | T/h | 21 | 23 | 24 | 16 |
| | Top C200 | | | | | |
| (17) | Top Temperature | °C. | 72 | 74 | 75 | 69 |
| (18) | Top flow rate | T/h | 16 | 17 | 18 | 11 |
| | Side take-off C200 | | | | | |
| (16) | Temperature | °C. | 91 | 91 | 91 | 91 |
| (16) | Technical acrylic acid flow rate | T/h | 5.6 | 5.6 | 5.6 | 5.0 |
| | Bottom C200 | | | | | |
| (20) | C200 bottom temperature | °C. | 99 | 97 | 98 | 101 |
| (20) | Bottom flow rate | T/h | 0.3 | 0.3 | 0.3 | 0.2 |
| | Acrylic acid recovery yield | | 98.1% | 99.9% | 99.9% | 86.2% |

The invention claimed is:

1. A process free of external organic solvent for recovering biobased acrylic acid from a gaseous reaction mixture obtained by gas-phase oxidation of a stream containing acrolein generated by a glycerol dehydration reaction in a first reactor, comprising the steps of:
   (i) subjecting the stream containing acrolein to separation, resulting in an aqueous phase substantially depleted of acrolein and a gaseous reaction mixture rich in acrolein and substantially depleted of water and methyglyoxal, thereby controlling water content,
   (ii) subjecting said gaseous reaction mixture rich in acrolein to a gas-phase catalytic oxidation reaction in a second reactor obtaining a gaseous reaction mixture wherein said gaseous reaction mixture comprises a water/acrylic acid weight ratio of less than 1.6,
   (iii) subjecting the gaseous reaction mixture from step (ii) comprising a water/acrylic acid weight ratio of less than 1.6 to dehydration in a first dehydration column, resulting in a dehydration column top stream, a part of which is condensed and returned to the dehydration column in the form of reflux, and to a dehydration column bottom stream;
   iv) at least partly distilling the dehydration column bottom stream in a second purification column, resulting in a purification column top stream which is at least partly condensed and returned to the dehydration column, and in a purification column bottom stream containing heavy compounds;
   v) recovering a final stream comprising more than 98% by weight of acrylic acid by side take-off from the purification column.

2. A process according to claim 1 wherein the gaseous reaction mixture comprises a water/acrylic acid weight ratio of between 0.3 and 1.5.

3. A process according to claim 1 wherein the gaseous reaction mixture is at least partially condensed using a condenser internal to the dehydration column and is optionally precooled.

4. A process according to claim 1 wherein the gaseous reaction mixture is at least partly condensed using a condenser external to the dehydration column and is optionally precooled.

5. A process according to claim 1 wherein at least part of the dehydration column bottom stream is sent to a heat exchanger, which may be a reboiler or a cooler, before being returned to the dehydration column.

6. A process according to claim 1 wherein part of the dehydration column bottom stream is brought into contact with the gaseous reaction mixture and the resulting stream is sent to step i).

7. A process according to claim 1 wherein the purification column top stream is at least partly sent to a condenser, the stream leaving the condenser being partly or totally returned to the dehydration column.

8. A process according to claim 1 wherein at least part of the dehydration column top stream is subjected to oxidation, and energy produced vaporizes glycerol prior to the dehydration reaction in the first reactor.

9. A process according to claim 1 wherein at least part of the purification column bottom stream is brought to a purification column heater/reboiler.

10. A process according to claim 1 wherein at least part of the purification column bottom stream is subjected to thermal cracking to produce acrylic acid.

11. A process according to claim 1 wherein at least part of the final stream taken off from the side of the purification column is subjected to crystallization.

12. The process according to claim 1 wherein separation of step i) is a partial condensation carried out at a pressure of between $10^5$ and $5 \times 10^5$ Pa, and at a temperature of between 40° C. and 90° C.

13. The process according to claim 1 wherein at least part of the aqueous phase depleted of acrolein of step i) is subjected to oxidation before being recycled and the energy produced vaporizes glycerol prior to the dehydration reaction.

* * * * *